(12) United States Patent
Patel

(10) Patent No.: US 11,813,371 B2
(45) Date of Patent: Nov. 14, 2023

(54) CURRENCY DISINFECTING ASSEMBLY

(71) Applicant: Jigar Patel, Louisville, KY (US)

(72) Inventor: Jigar Patel, Louisville, KY (US)

(*) Notice: Subject to any disclaimer, the term of this patent is extended or adjusted under 35 U.S.C. 154(b) by 310 days.

(21) Appl. No.: 17/224,634

(22) Filed: Apr. 7, 2021

(65) Prior Publication Data

US 2022/0323622 A1    Oct. 13, 2022

(51) Int. Cl.
*A61L 2/10* (2006.01)

(52) U.S. Cl.
CPC .............. *A61L 2/10* (2013.01); *A61L 2202/11* (2013.01); *A61L 2202/14* (2013.01)

(58) Field of Classification Search
CPC ......... A61L 2/10; A61L 2/26; A61L 2202/122
See application file for complete search history.

(56) References Cited

U.S. PATENT DOCUMENTS

| | | | |
|---|---|---|---|
| 7,331,366 B1* | 2/2008 | Patterson | A45C 13/1092 |
| | | | 150/147 |
| 2003/0034459 A1 | 2/2003 | Bonin | |
| 2010/0266445 A1 | 10/2010 | Campagna | |
| 2011/0925356 | 10/2011 | Goldman | |
| 2013/0045133 A1* | 2/2013 | Maguire | A61L 2/24 |
| | | | 422/1 |
| 2016/0343214 A1 | 11/2016 | Chap | |
| 2017/0035923 A1 | 2/2017 | Yanke | |
| 2021/0299304 A1* | 9/2021 | Concannon | A61L 2/26 |

\* cited by examiner

*Primary Examiner* — Eliza W Osenbaugh-Stewart

(57) ABSTRACT

A currency disinfecting assembly for sterilizing paper currency includes a cabinet that is comprised of an opaque material to inhibit light from passing therethrough. A plurality of holders is each disposed in an interior of the cabinet to accommodate paper currency. A plurality of light emitters is each coupled to the cabinet to emit light outwardly therefrom. Each of the light emitters is positioned inside of the cabinet to direct the light onto the paper currency. Moreover, each of the light emitters emits light in the ultraviolet spectrum to sterilize the paper currency.

7 Claims, 8 Drawing Sheets

CURRENCY DISINFECTING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to disinfecting devices and more particularly pertains to a new disinfecting device for sterilizing paper currency. The device includes a plurality of ultraviolet lights within a cabinet and a plurality of elongated holders in the cabinet. Each of the elongated holders holds paper currency that is sterilized with ultraviolet light.

(2) Description of Related Art Including Information Disclosed Under 37 CFR 1.97 and 1.98

The prior art relates to disinfecting devices including a variety of housings that have ultraviolet lights therein for sterilizing objects. In no instance does the prior art disclose a cabinet with a plurality of holders mounted therein for holding paper currency and a plurality of ultraviolet lights for sterilizing the paper currency.

BRIEF SUMMARY OF THE INVENTION

An embodiment of the disclosure meets the needs presented above by generally comprising a cabinet that is comprised of an opaque material to inhibit light from passing therethrough. A plurality of holders is each disposed in an interior of the cabinet to accommodate paper currency. A plurality of light emitters is each coupled to the cabinet to emit light outwardly therefrom. Each of the light emitters is positioned inside of the cabinet to direct the light onto the paper currency. Moreover, each of the light emitters emits light in the ultraviolet spectrum to sterilize the paper currency.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
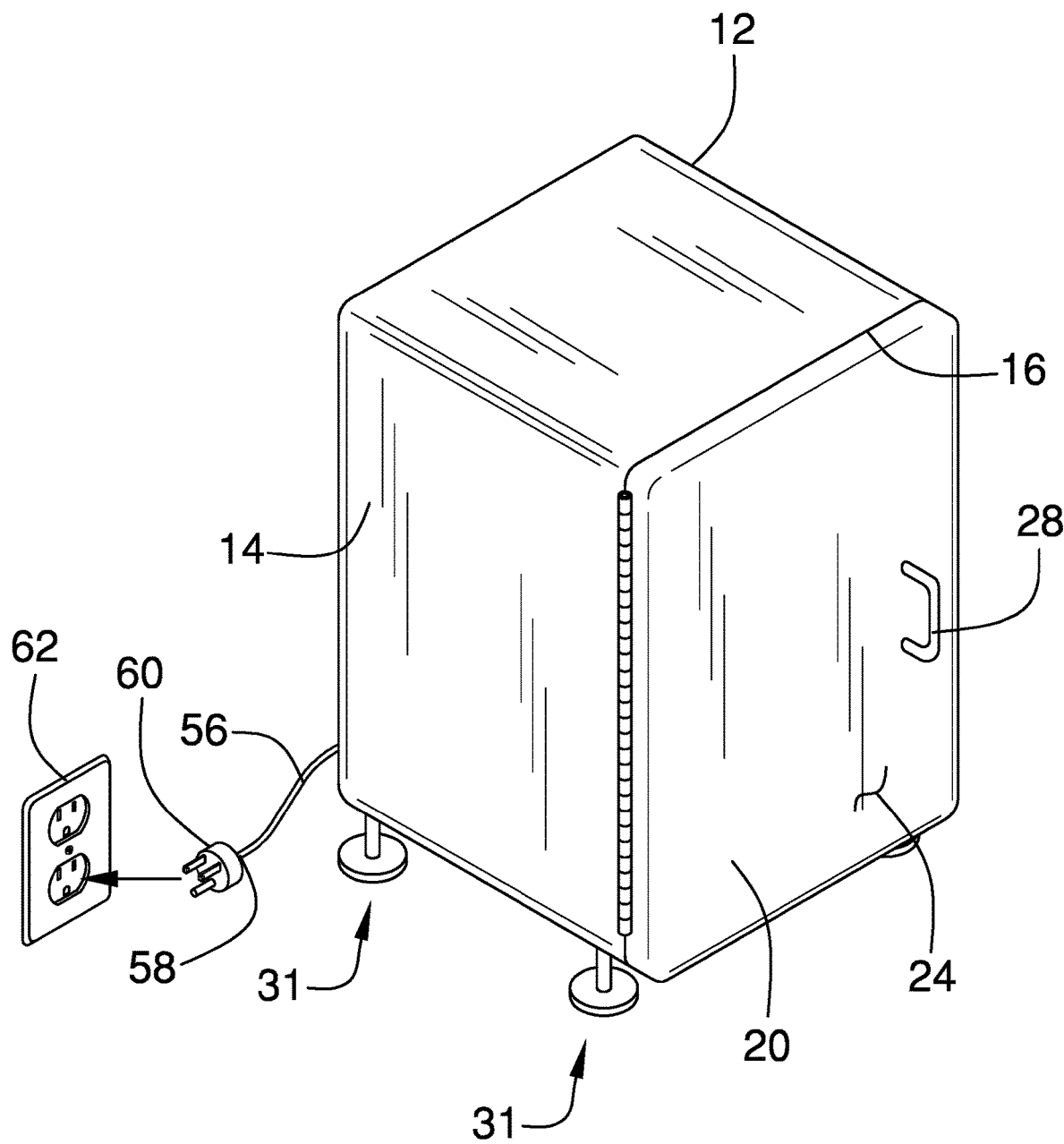
FIG. 1 is a front perspective view of a currency disinfecting assembly according to an embodiment of the disclosure.
Figure 2:
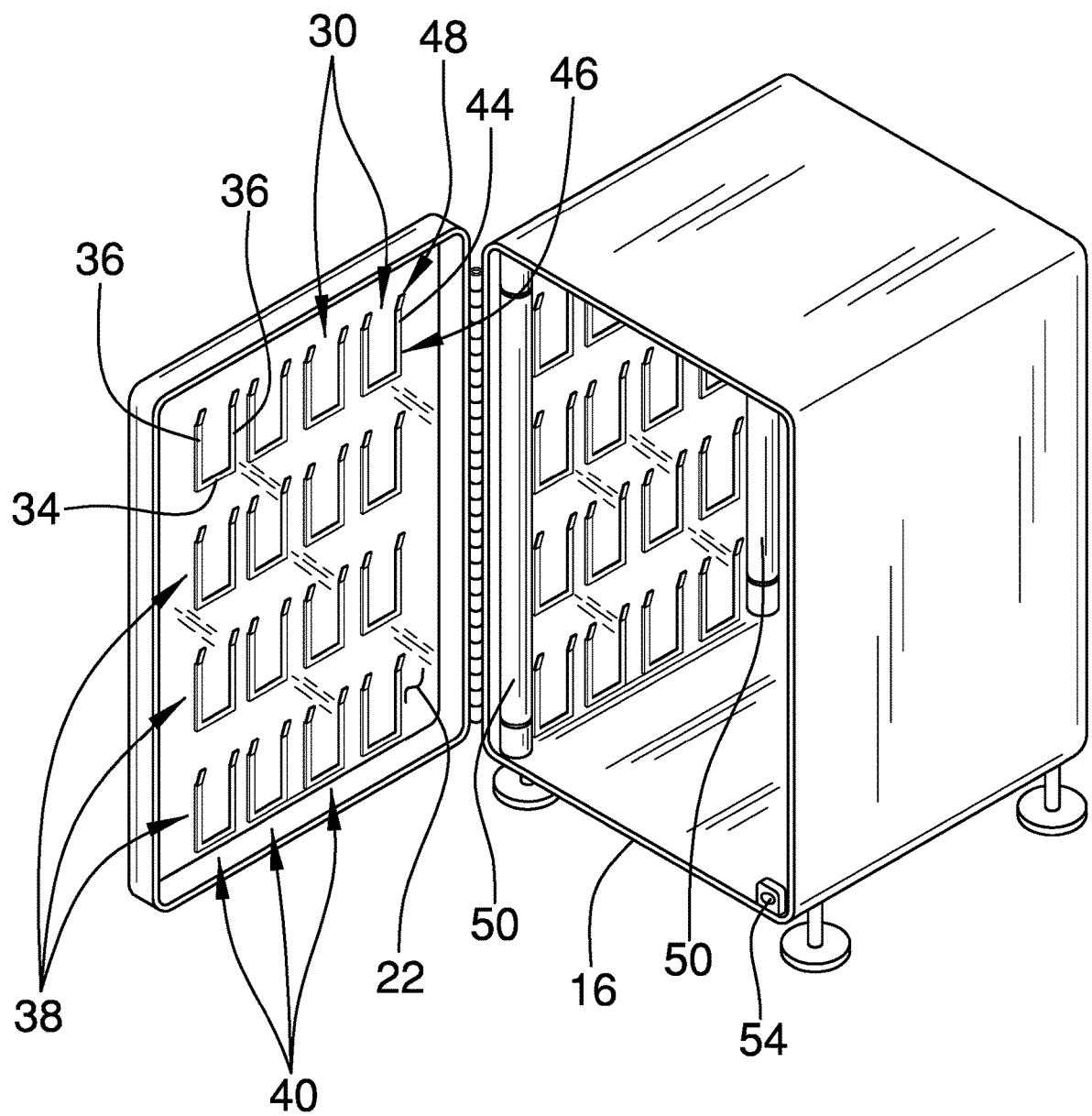
FIG. 2 is a perspective view of an embodiment of the disclosure showing a door in an open position.
Figure 3:
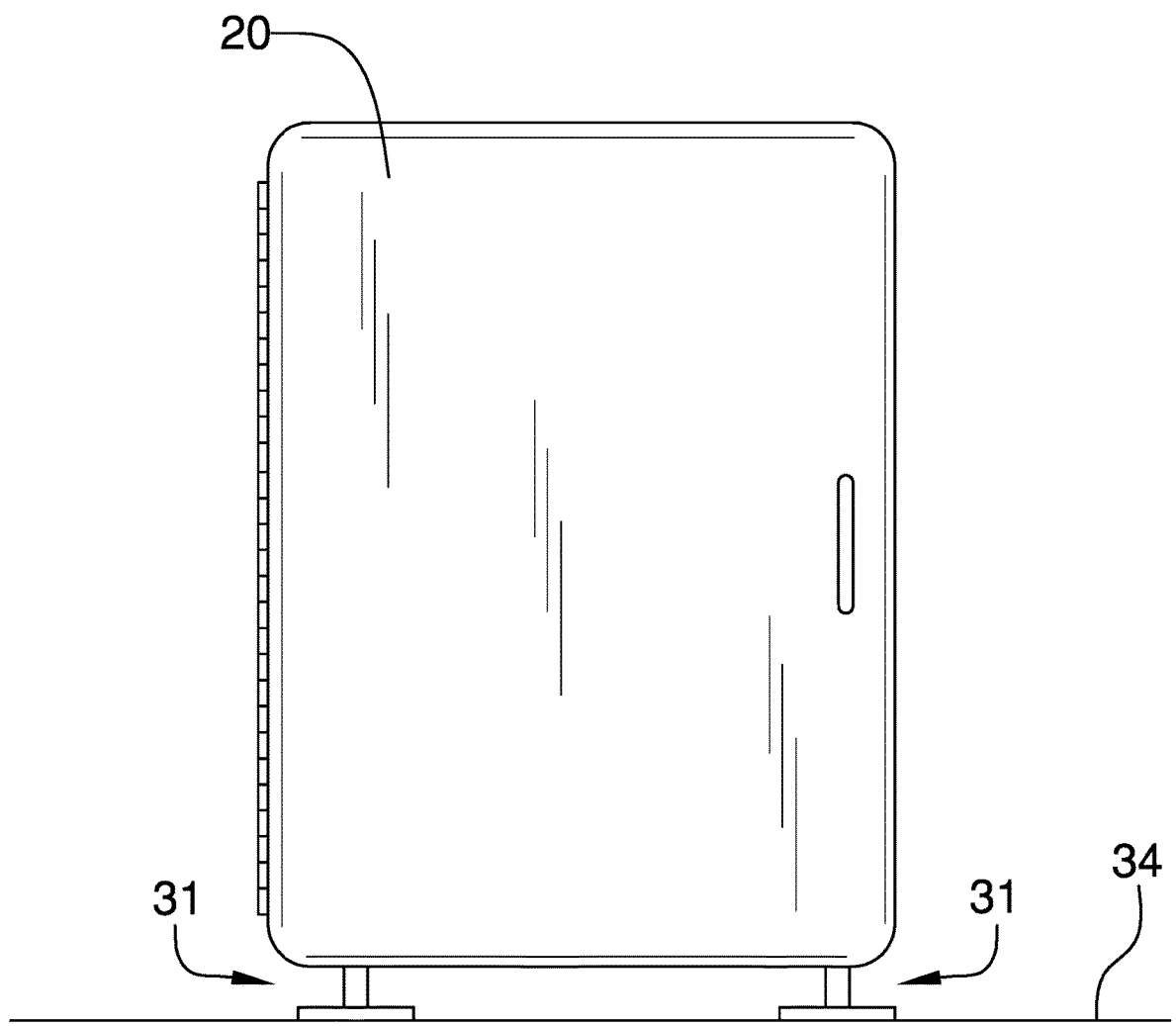
FIG. 3 is a front view of an embodiment of the disclosure.
Figure 4:
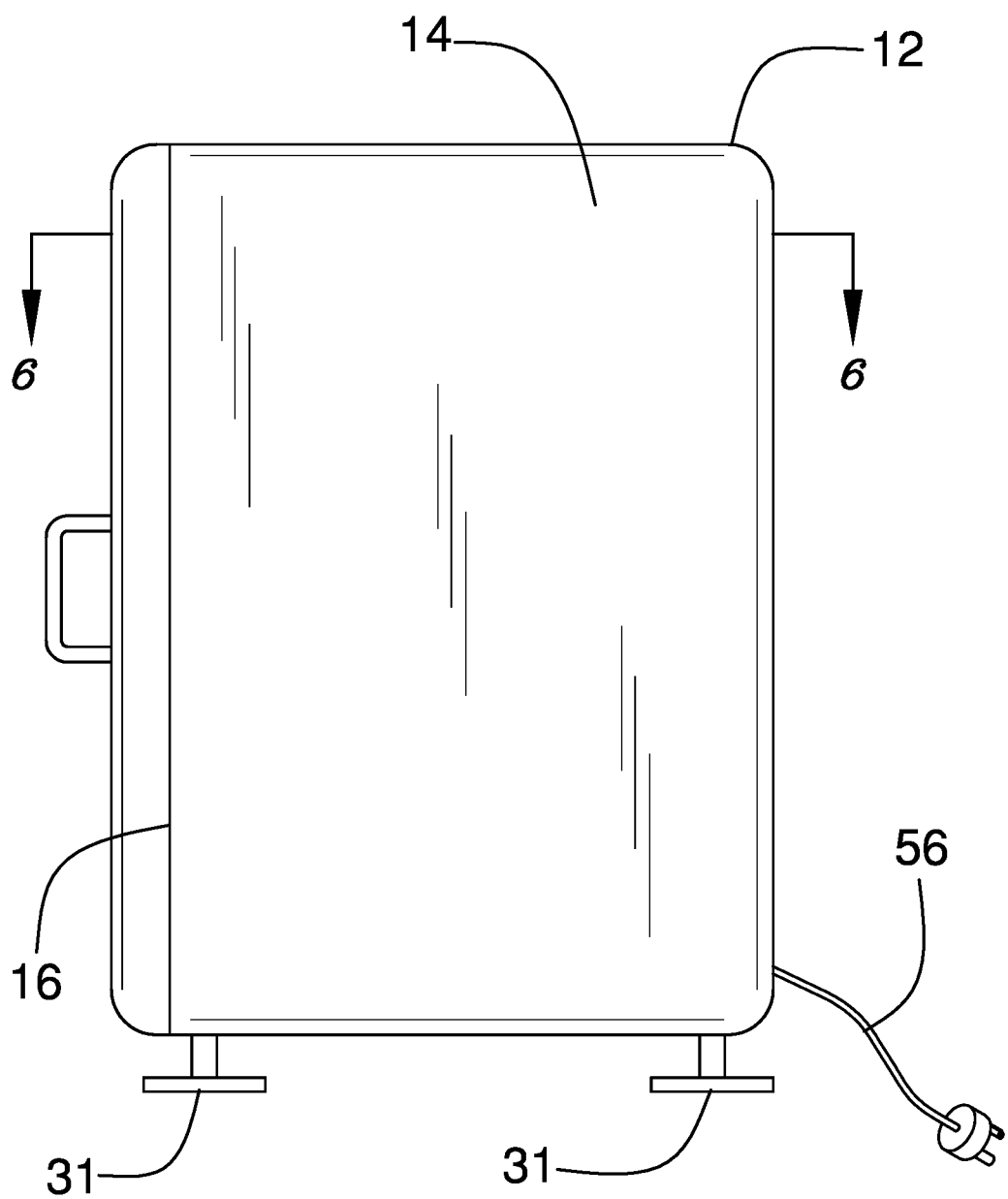
FIG. 4 is a left side view of an embodiment of the disclosure.
Figure 5:
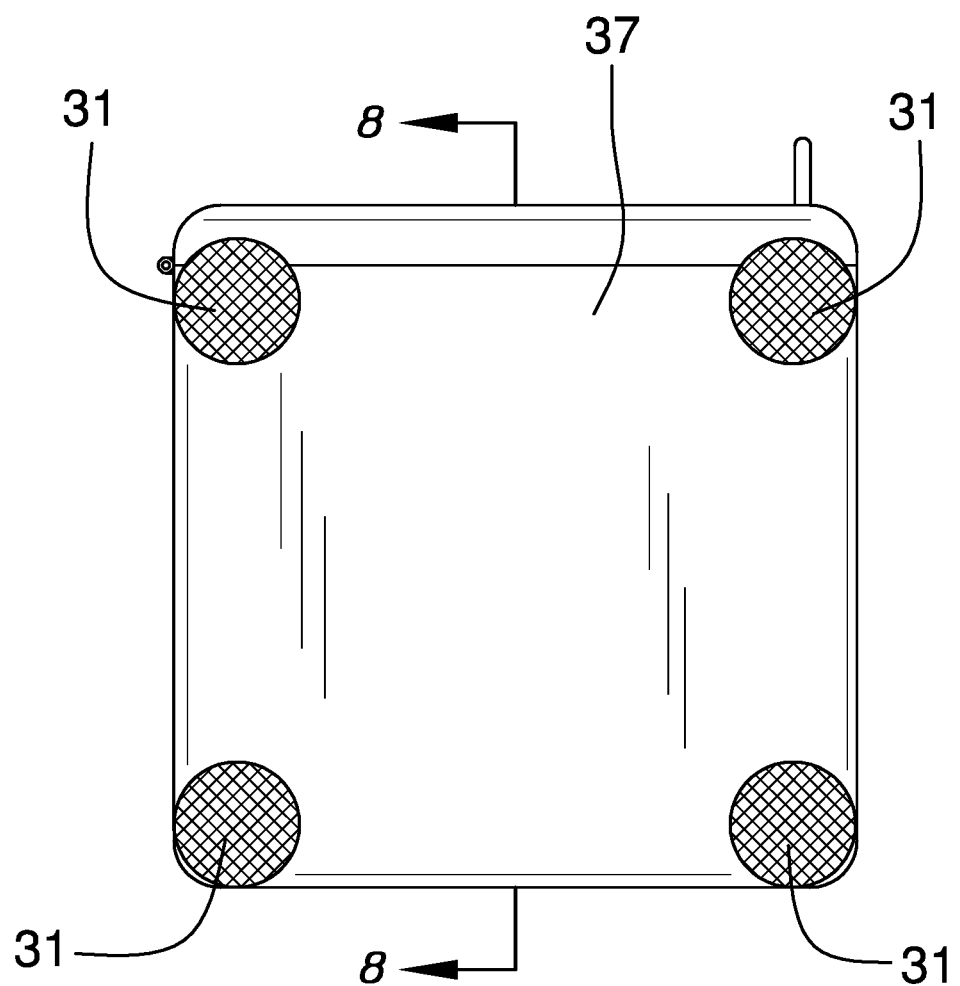
FIG. 5 is a bottom view of an embodiment of the disclosure.
Figure 6:
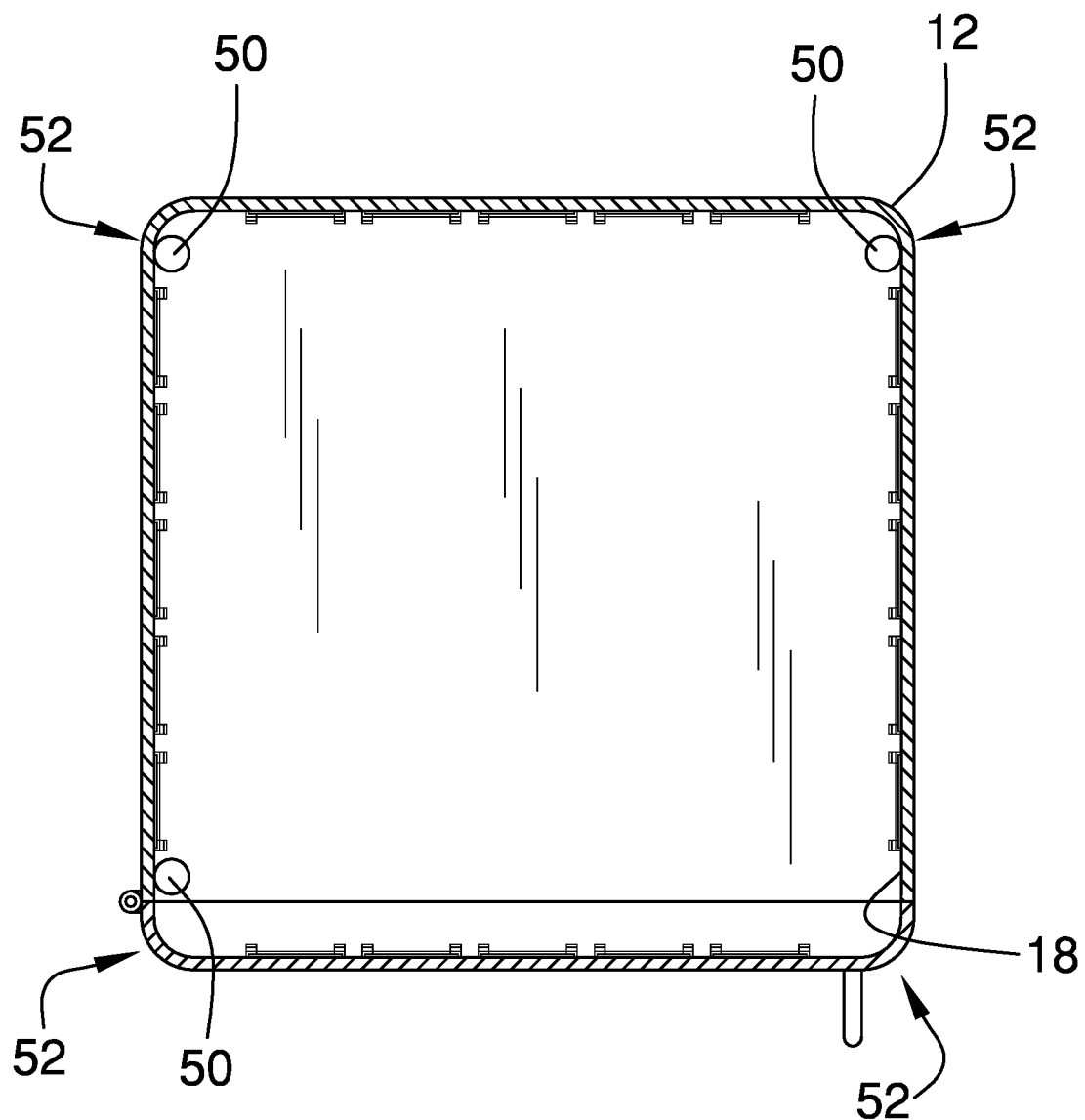
FIG. 6 is a cross sectional view taken along line 6-6 of FIG. 4 of an embodiment of the disclosure.
Figure 7:
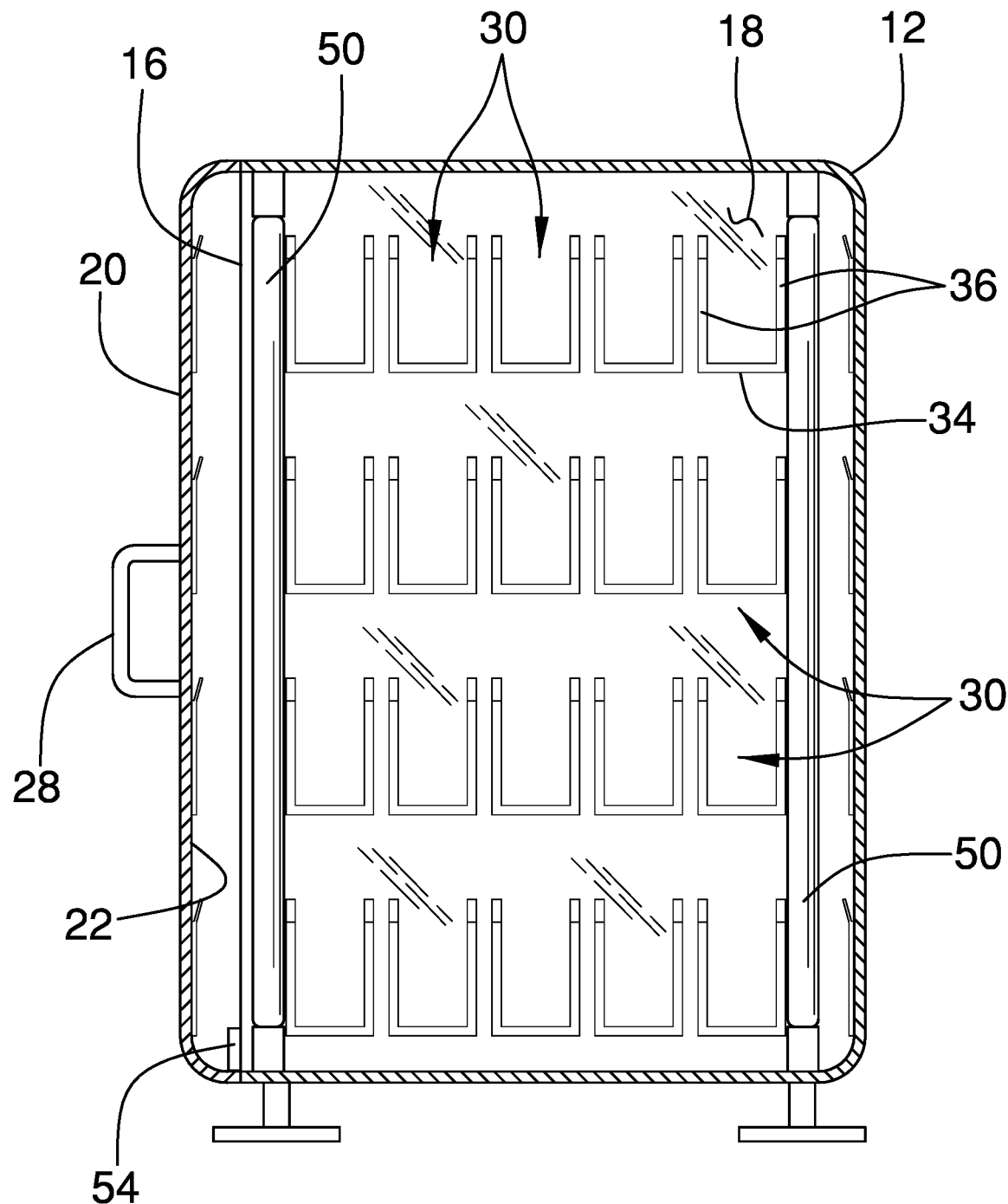
FIG. 7 is a left side cut-away view of an embodiment of the disclosure.
Figure 8:
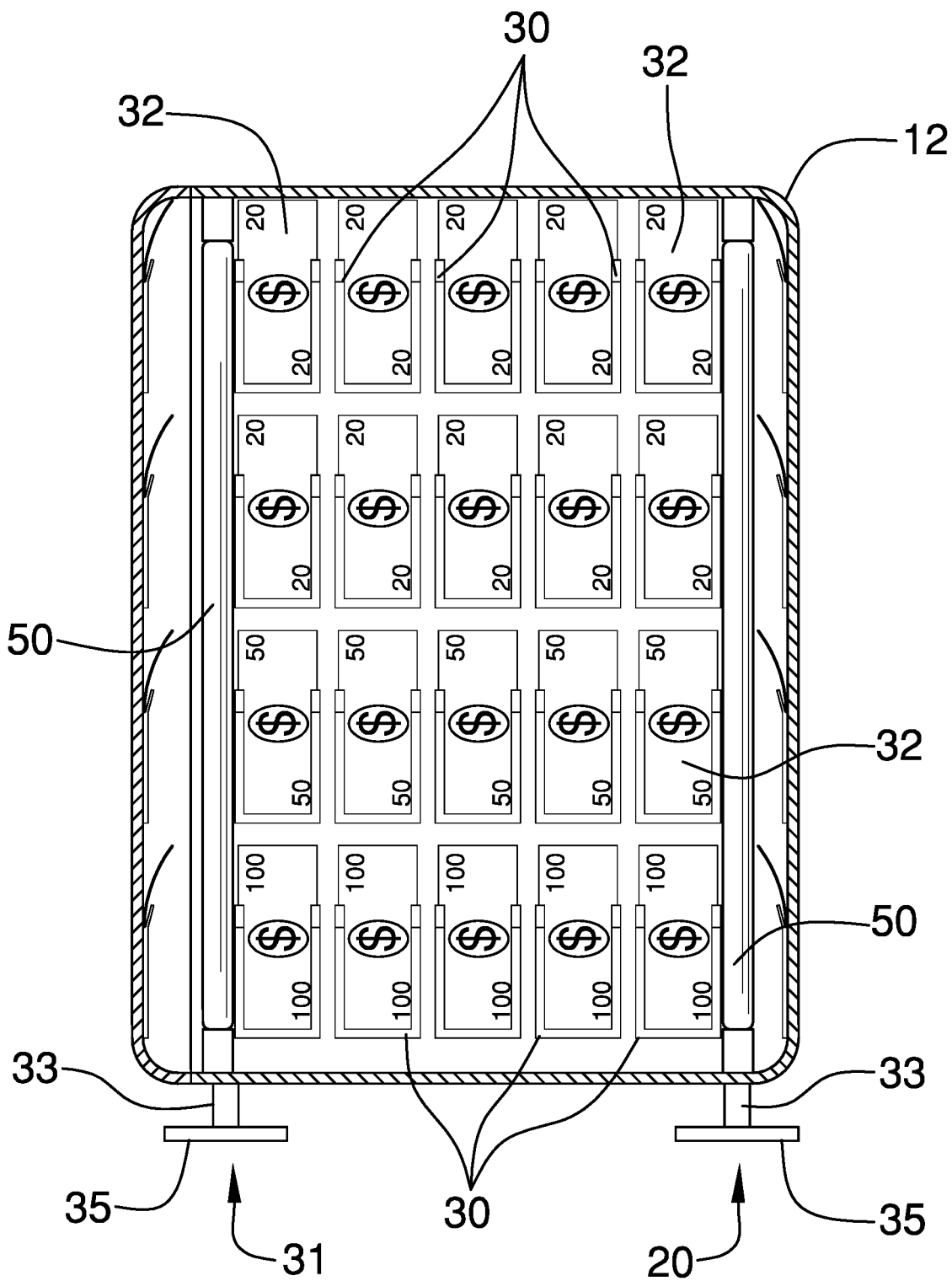
FIG. 8 is a cross sectional view taken along line 8-8 of FIG. 5 of an embodiment of the disclosure.

With reference now to the drawings, and in particular to FIGS. 1 through 8 thereof, a new disinfecting device embodying the principles and concepts of an embodiment of the disclosure and generally designated by the reference numeral 10 will be described.

As best illustrated in FIGS. 1 through 8, the currency disinfecting assembly 10 generally comprises a cabinet 12 that is comprised of an opaque material to inhibit light from passing therethrough. The opaque material may be plastic, metal, wood or other type of rigid, planar material. The cabinet 12 has an outer wall 14, the outer wall 14 has a front side 16 and the front side 16 is open into an interior of the cabinet 12. The outer wall 14 has an inside surface 18 and the inside surface 18 is comprised of a light reflecting material to reflect light. A door 20 is hingedly coupled to the cabinet 12, and the door 20 has a rear surface 22, a front surface 24 and a first edge 26. The first edge 26 is hingedly coupled to the front side 16 of the outer wall 14 of the cabinet 12. Additionally, the rear surface 22 is comprised of a light reflecting material to reflect light, and the rear surface 22 is directed into the interior of the cabinet 12 when the door 20 is closed. The inside surface 18 of the cabinet 12 and the rear surface 22 of the door 20 may comprise a mirror, polished steel or other similar type of highly reflective material. A handle 28 is coupled to the front surface 24 of the door 20 and the handle 28 can be gripped for opening and closing the door 20.

A plurality of holders 30 is provided and each of the holders 30 is disposed in an interior of the cabinet 12. Each of the holders 30 is elongated to accommodate paper currency 32. Each of the holders 30 comprises a lower member 34 extending between a pair of upright members 36. The upright members 36 are spaced apart from each other and are oriented parallel to each other such that each of the holders 30 has a U-shape. The lower member 34 and each of the upright members 36 is coupled to the inside surface 18 of the outer wall 14 of the cabinet 12. A plurality of feet 31, each including a stem 33 and a pad 35 coupled to the stem 33, is each coupled to a lower side 37 of the outer wall 14 of the cabinet 12. The stem 33 is attached to the lower side 37 such that the pad 35 can rest on a support surface 39.

Each of the upright members 36 of each of the holders 30 is vertically oriented and the holders 30 is arranged into a plurality of rows 38 and columns 40 on the inside surface 18. Additionally, each of the upright members 36 of each of the holders 30 has a distal end 42 with respect to the lower member 34. Each of the upright members 36 has a bend 44 thereon to define a lower portion 46 forming an angle with an upper portion 48, and the distal end 42 of each of the upright members 36 is associated with the upper portion 48. Moreover, the upper portion 48 of each of the upright members 36 angles away from the inside surface 18 of the outer wall 14 to facilitate the paper currency 32 to be inserted into the holders 30. Respective ones of the plurality of holders 30 are positioned on the rear surface 22 of the door 20.

A plurality of light emitters 50 is provided and each of the light emitters 50 is coupled to the cabinet 12 to emit light outwardly therefrom. Each of the light emitters 50 is positioned inside of the cabinet 12 thereby facilitating each of the light emitters 50 to direct the light onto the paper currency 32. Moreover, each of the light emitters 50 emits light in the ultraviolet spectrum to sterilize the paper currency 32. Each of the light emitters 50 is elongated and each of the light emitters 50 is vertically oriented. Additionally, each of the light emitters 50 is aligned with a respective one of four corners 52 of the outer wall 14 of the cabinet 12. Each of the light emitters 50 may comprise a fluorescent light, a light emitting diode, or other type of electronic light emitter that emits ultraviolet light at sufficient intensity to kill bacteria and viruses. Additionally, the inside surface 18 of the outer wall 14 of the cabinet 12 and the rear surface 22 of the door 20 reflect the light emitted by the light emitters 50 to facilitate both sides of the paper currency 32 to be sterilized.

A switch 54 is coupled to the cabinet 12 and the switch 54 is aligned with the door 20. The door 20 turns the switch 54 on when the door 20 is closed and the switch 54 is turned off when the door 20 is opened. Additionally, the switch 54 is electrically coupled to the light emitters 50 for turning the light emitters 50 of and off. A power cord 56 is coupled to and extends away from the cabinet 12 and the power cord 56 is electrically coupled to the switch 54. The power cord 56 has a distal end 58 with respect to the cabinet 12 and a male plug 60 is electrically coupled to the distal end 42. The male plug 60 engages a power source 62 comprising a female electrical outlet.

In use, paper currency 32 is positioned into each of the holders 30 and the door 20 is closed. Thus, the light emitters 50 are turned on to sterilize the paper currency 32 in the holders 30. In this way the paper currency 32 is less likely to transfer infectious bacteria or viruses between people. The door 20 is opened after being closed for at least two minutes to ensure the paper currency 32 is fully sterilized and the paper currency 32 is removed from each of the holders 30. In this way businesses such as casinos, restaurants, bars and other businesses that typically handle large amounts of cash can quickly and easily sterilize the cash that they handle.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A currency disinfecting assembly for disinfecting paper currency thereby reducing the transmission of bacteria on the paper currency, said assembly comprising:
   a cabinet being comprised of an opaque material wherein said cabinet is configured to inhibit light from passing therethrough, wherein said cabinet has an outer wall, said outer wall having a front side, said front side being open into an interior of said cabinet, said outer wall having an inside surface, said inside surface being comprised of a light reflecting material wherein said inside surface is configured to reflect light;
   a plurality of holders, each of said holders being disposed in an interior of said cabinet, each of said holders being elongated wherein each of said holders is configured to accommodate paper currency;
   a plurality of light emitters, each of said light emitters being coupled to said cabinet wherein each of said light emitters is configured to emit light outwardly therefrom, each of said light emitters being positioned inside of said cabinet wherein each of said light emitters is configured to direct the light onto the paper currency, each of said light emitters emitting ultraviolet radiation wherein each of said light emitters is configured to sterilize the paper currency; and
   wherein each of said holders comprises a lower member extending between a pair of upright members, said upright members being spaced apart from each other and being oriented parallel to each other such that each of said holders has a U-shape, said lower member and each of said upright members being coupled to said inside surface of said outer wall of said cabinet, each of said upright members of each of said holders being vertically oriented, said holders being arranged into a plurality of rows and columns on said inside surface.

2. The assembly according to claim 1, further comprising a door being hingedly coupled to said cabinet, said door having a rear surface, a front surface and a first edge, said first edge being hingedly coupled to said front side of said outer wall of said cabinet, said rear surface being comprised of a light reflecting material wherein said rear surface is configured to reflect light, said rear surface being directed into said interior of said cabinet when said door is closed.

3. The assembly according to claim 2, further comprising a switch being coupled to said cabinet, said switch being aligned with said door, said door turning said switch on when said door is closed, said switch being turned off when said door is opened, said switch being electrically coupled to said light emitters for turning said light emitters of and off.

4. The assembly according to claim 1, wherein each of said upright members of each of said holders has a distal end with respect to said lower member, each of said upright members having a bend thereon to define a lower portion forming an angle with an upper portion, said distal end of each of said upright members being associated with said upper portion.

5. The assembly according to claim 4, wherein said upper portion of each of said upright members angles away from said inside surface of said outer wall wherein said upper portion of each of said upright members of each of said holders is configured to facilitate the paper currency to be inserted into said holders, respective ones of said plurality of holders being positioned on said rear surface of said door.

6. The assembly according to claim 1, wherein each of said light emitters is elongated, each of said light emitters being vertically oriented, each of said light emitters being aligned with a respective one of four corners of said outer wall of said cabinet.

7. A currency disinfecting assembly for disinfecting paper currency thereby reducing the transmission of bacteria on the paper currency, said assembly comprising:
   a cabinet being comprised of an opaque material wherein said cabinet is configured to inhibit light from passing therethrough, said cabinet having an outer wall, said outer wall having a front side, said front side being open into an interior of said cabinet, said outer wall having an inside surface, said inside surface being comprised of a light reflecting material wherein said inside surface is configured to reflect light;
   a door being hingedly coupled to said cabinet, said door having a rear surface, a front surface and a first edge, said first edge being hingedly coupled to said front side of said outer wall of said cabinet, said rear surface being comprised of a light reflecting material wherein said rear surface is configured to reflect light, said rear surface being directed into said interior of said cabinet when said door is closed;
   a plurality of holders, each of said holders being disposed in an interior of said cabinet, each of said holders being elongated wherein each of said holders is configured to accommodate paper currency, each of said holders comprising a lower member extending between a pair of upright members, said upright members being spaced apart from each other and being oriented parallel to each other such that each of said holders has a U-shape, said lower member and each of said upright members being coupled to said inside surface of said outer wall of said cabinet, each of said upright members of each of said holders being vertically oriented, said holders being arranged into a plurality of rows and columns on said inside surface, each of said upright members of each of said holders having a distal end with respect to said lower member, each of said upright members having a bend thereon to define a lower portion forming an angle with an upper portion, said distal end of each of said upright members being associated with said upper portion, said upper portion of each of said upright members angling away from said inside surface of said outer wall wherein said upper portion of each of said upright members of each of said holders is configured to facilitate the paper currency to be inserted into said holders, respective ones of said plurality of holders being positioned on said rear surface of said door;
   a plurality of light emitters, each of said light emitters being coupled to said cabinet wherein each of said light emitters is configured to emit light outwardly therefrom, each of said light emitters being positioned inside of said cabinet wherein each of said light emitters is configured to direct the light onto the paper currency, each of said light emitters emitting ultraviolet radiation wherein each of said light emitters is configured to sterilize the paper currency, each of said light emitters being elongated, each of said light emitters being vertically oriented, each of said light emitters being aligned with a respective one of four corners of said outer wall of said cabinet;
   a switch being coupled to said cabinet, said switch being aligned with said door, said door turning said switch on when said door is closed, said switch being turned off when said door is opened, said switch being electrically coupled to said light emitters for turning said light emitters of and off; and
   a power cord being coupled to and extending away from said cabinet, said power cord being electrically coupled to said switch, said power cord having a distal end with respect to said cabinet, said distal end having a male plug being electrically coupled thereto, said male plug engaging a power source comprising a female electrical outlet.

* * * * *